(12) United States Patent
Pye et al.

(10) Patent No.: US 6,395,894 B2
(45) Date of Patent: *May 28, 2002

(54) PROCESS FOR THE SYNTHESIS OF CARBAPENEM INTERMIDIATES, AND COMPOUNDS PRODUCED

(76) Inventors: Philip J. Pye; Paul J. Reider; Kai Rossen; Ralph P. Volante, all of c/o Merck & Co., Inc., P.O. Box 2000, Rahway, NJ (US) 07065-0900

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/292,257

(22) Filed: Apr. 15, 1999

Related U.S. Application Data

(60) Provisional application No. 60/082,003, filed on Apr. 16, 1998, and provisional application No. 60/091,422, filed on Jul. 1, 1998.

(51) Int. Cl.[7] ................... C07D 477/14; C07D 205/08; C07F 9/18
(52) U.S. Cl. ........................................ 540/200; 540/302
(58) Field of Search .................................. 540/302, 200

(56) References Cited

U.S. PATENT DOCUMENTS 5,756,725 A    5/1998   Wilkening et al. .......... 540/302

FOREIGN PATENT DOCUMENTS

| EP | 0 102 239 A1 | 3/1984 |
| EP | 0 102 239 B1 | 3/1987 |
| EP | 0 212 404 A1 | 3/1987 |
| EP | 0 330 018    | 8/1989 |
| EP | 0 476 649 A2 | 3/1992 |
| EP | 330108       | 12/1995 |
| EP | 0 695 753 A1 | 2/1996 |
| EP | 573667       | 6/2001 |

*Primary Examiner*—Mark L. Berch
(74) *Attorney, Agent, or Firm*—Sylvia A. Ayler; Mark R. Daniel

(57) ABSTRACT

A process of synthesizing a compound of structural formula 6

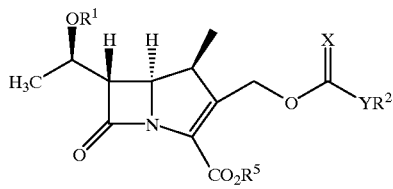

is disclosed wherein $R^1$ represents H or a suitable protecting group for an alcohol; $R^2$ represents a benzyl, $C_{1-6}$ alkyl or aryl; Y represents $C_{1-3}$ alkyl, O, NH or S; X represents O, NH, or S and $R^5$ represents a carboxy protecting group, comprising reacting a compound of formula 5:

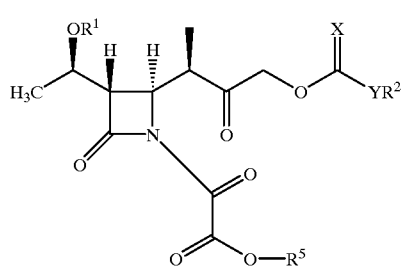

wherein $R^1$, $R^2$, $R^5$, X and Y are as previously described with a phosphite or phosphonite reagent to produce a compound of formula 6. Further disclosed is an efficient method for the synthesis of a compound of formula 2:

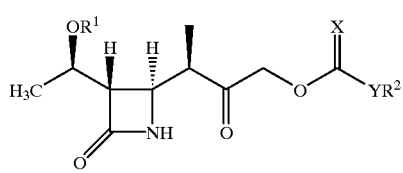

which comprises reacting a 4-acyl-2-azetidinone with a titanium, zirconium or hafnium enolate of a 1-hydroxy-2-butanone derivative.

29 Claims, No Drawings

US 6,395,894 B2

1

PROCESS FOR THE SYNTHESIS OF CARBAPENEM INTERMIDIATES, AND COMPOUNDS PRODUCED

This application claims the benefit of U.S. Provisional Application No. 60/082,003, filed Apr. 16, 1998 and U.S. Provisional Application No. 60/091,422, filed Jul. 1, 1998.

BACKGROUND OF THE INVENTION

The present invention relates to a process for synthesizing 1-β-methyl-2-hydroxymethyl carbapenem intermediates. Generally the carbapenems are substituted at the 2-position. The intermediate compounds are included as well.

European applications 0330108, 0102239, 0212404, 0695753 and 0476649 disclose methods for synthesizing various antibiotic derivatives.

Many of the carbapenems are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). These antibacterials thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The invention describes a short and high yielding synthesis of protected 1-β-methyl-2-hydroxymethyl substituted carbapenems as key intermediates for the synthesis of anti-MRSA carbapenem antibiotics. The synthesis involves a highly diastereoselective addition of a titanium, zirconium or hafnium enolate of a suitably protected 1-hydroxy-2-butanone derivative with 4-acyl-2-azetidinone. Using this enolate, the resulting derivatized 2-azetidinone product is obtained largely as a single diastereomer rather than a mixture. Additionally, the two chiral centers which are produced are of the correct absolute stereochemical configuration for subsequent synthesis of 1-β-methyl-2-hydroxymethyl substituted carbapenems.

In one aspect of the invention, a process of synthesizing a compound of formula 2:

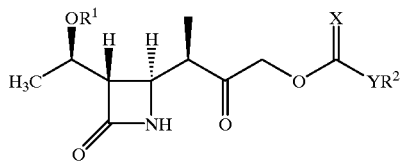

2 is disclosed wherein $R^1$ represents H or a suitable protecting group for an alcohol; $R^2$ represents a benzyl, $C_{1-6}$ alkyl or aryl; Y represents $C_{1-3}$ alkyl, O, NH or S; and X represents O, NH, or S comprising reacting a compound of formula 1:

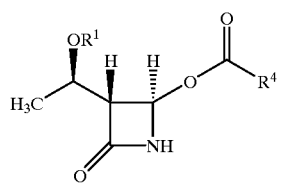

wherein $R^1$ is described above and $R^4$ represents $C_{1-15}$ alkyl, aryl or $C_{1-6}$ aralkyl;

with a compound of formula 3:

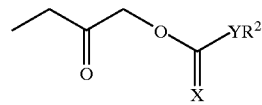

wherein $R^2$, X and Y are as previously defined in the presence of $WZ_4$ and an amine to produce a compound of formula 2, wherein W is a titanium, zirconium or hafnium metal and Z represents halo, sulfonate, alkoxy, aryloxy or combination thereof.

DETAILED DESCRIPTION OF THE INVENTION

The present invention relates to a process for making protected 1-β-methyl-2-hydroxymethyl substituted carbapenems which are key intermediates in the synthesis of anti-MRSA carbapenem antibiotics (such as those disclosed in U.S. Ser. No. 08/825,786 filed on Apr. 8, 1997 now U.S. Pat. No. 5,756,725, the teachings of which are hereby incorporated by reference). The intermediates can be readily coupled to a wide range of functional groups (see U.S. Ser. No. 08/825,786 now U.S. Pat. No. 5,756,725).

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a species of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like as well as rings which are fused, e.g., naphthyl, phenanthrenyl and the like. An aryl group thus contains at least one ring having at least 5 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

Aryl also refer to heteroaryl, which is a monocyclic aromatic hydrocarbon group having 5 or 6 ring atoms, or a polycyclic aromatic group having 8 to 16 atoms, containing at least one heteroatom, O, S, S(O), $SO_2$ or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole and the like.

As used herein, "aralkyl" is intended to mean an aryl or heteroaralkyl moiety, as defined above, attached through a $C_{1-6}$ alkyl linker, where alkyl is defined above. Examples of aralkyls include, but are not limited to, benzyl, naphtylmethyl, phenylpropyl, 2-pyridylmethyl, 2-imidazolylethyl, 2-quinolinylmethy, 2-imidazolylmethyl and the like.

Examples of polycyclic heteroaromatics include benzopyrans, benzofurans, benzopyrroles, benzimidazoles, benzothiazoles, quinolines, purines, isoquinolines, benzopyrimidines, dibenzofurans, dibenzothiophenes, 1,8-naphthosultams.

The term "heterocycle" (heterocyclyl) refers to a 5–16 membered cycloalkyl group (nonaromatic) with 1–4 rings, in which one of the carbon atoms in the ring is replaced by a heteroatom selected from O, S or N, and in which up to three additional carbon atoms may be replaced by heteroatoms.

The term "heteroatom" means O, S, S(O), $S(O)_2$ or N, selected on an independent basis.

Halogen and "halo" refer to bromine, chlorine, fluorine and iodine.

When a group is termed "protected", such as $R^1$, $R^5$ and the like, this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the compounds of the present invention, $R^1$ and $R^5$ represent alcohol and carboxyl protecting groups, respectively. Likewise, Y may represent a protecting group for X, which in turn represents O or N. These groups are generally removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups $R^5$ include allyl, benzhydryl, 2-naphthylmethyl, benzyl, silyl groups such as t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl (pNB), 4-pyridylmethyl and t-butyl, preferably pNB and benzyl.

Examples of suitable alcohol protecting groups $R^1$ include hydrogen, trialkylsilyl, diarylalkylsilyl, aryldialkylsilyl or trityl such as TMS, TES, TBDMS, alkyl carbonates such as benzyl carbonate, allyl carbonate, benzyl ether, diarylalkylsilyl, aryldialkylsilyl & trityl and the like. Preferred $R^1$ groups are trialkylsilyl or hydrogen.

Another aspect of the process that is of particular interest is the synthesis of a compound of formula 5:

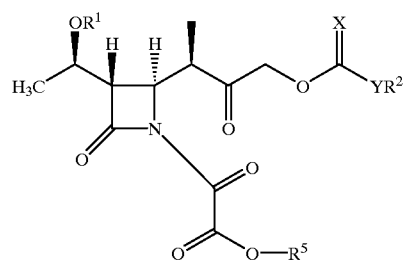

wherein $R^1$ represents H or a suitable protecting group for an alcohol; $R^2$ represents a benzyl, $C_{1-6}$ alkyl or aryl; Y represents $C_{1-3}$ alkyl, O, NH or S; X represents O, NH, or S and $R^5$ represents a carboxy protecting group, comprising reacting a compound of formula 2:

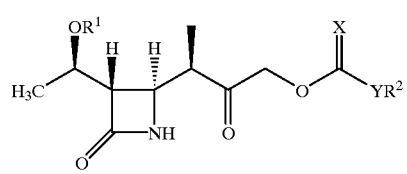

wherein $R^1$, $R^2$, X and Y are as previously described, with an activated oxalic acid agent in the presence of a base to produce a compound of formula 5.

In another aspect of the invention a process for synthesizing a compound of structural formula 6

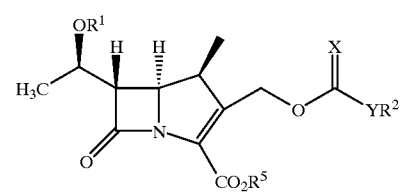

is disclosed wherein $R^1$ represents H or a suitable protecting group for an alcohol; $R^2$ represents a benzyl, $C_{1-6}$ alkyl or aryl; Y represents $C_{1-3}$ alkyl, O, NH or S; X represents O, NH, or S and $R^5$ represents a carboxy protecting group, comprising reacting a compound of formula 5:

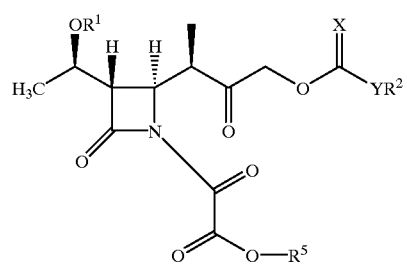

wherein $R^1$, $R^2$, $R^5$, X and Y are as previously described with a phosphite or phosphonite reagent to produce a compound of formula 6.

Another aspect of the process that is of interest is the synthesis of a carbapenem compound of formula 6

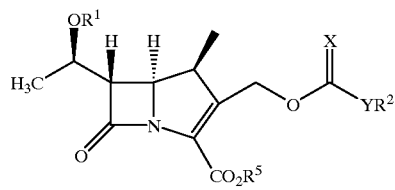

wherein $R^1$ represents H or a suitable protecting group for an alcohol; $R^2$ represents a benzyl, $C_{1-6}$ alkyl or aryl; Y represents $C_{1-3}$ alkyl, O, NH or S; X represents O, NH, or S and $R^5$ represents a carboxy protecting group, comprising reacting a compound of formula 2:

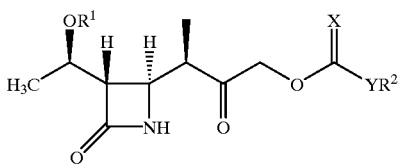

wherein $R^1$, $R^2$, X and Y are as previously described, with an activated oxalic acid agent in the presence of a base to produce a compound of formula 5

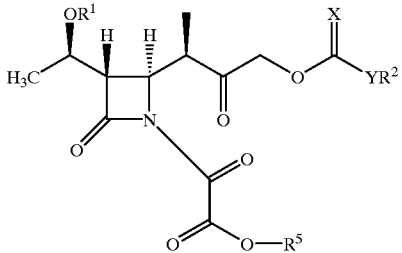

and reacting a compound of formula 5, wherein $R^1$, $R^2$, $R^5$, X and Y are as previously described with a phosphite or phosphonite reagent to produce a compound of formula 6.

Another aspect of the process that is of interest is the synthesis of a carbapenem compound of formula 6

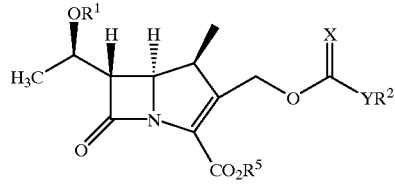

wherein $R^1$ represents H or a suitable protecting group for an alcohol; $R^2$ represents a benzyl, $C_{1-6}$ alkyl or aryl; Y represents $C_{1-3}$ alkyl, O, NH or S; X represents O, NH, or S and $R^5$ represents a carboxy protecting group, comprising reacting a compound of formula 1:

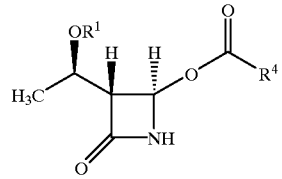

wherein $R^1$ is described above and $R^4$ represents $C_{1-15}$ alkyl, aryl or $C_{1-6}$ aralkyl;
with a compound of formula 3:

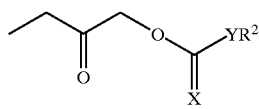

wherein $R^2$, X and Y are as previously defined in the presence of $WZ_4$ and an amine to produce a compound of formula 2:

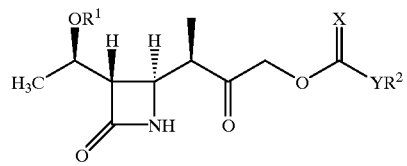

wherein W is a titanium, zirconium or hafnium metal and Z represents halo, sulfonate, alkoxy, aryloxy or combination thereof, and $R^1$, $R^2$, X and Y are as previously described, reacting a compound of formula 2 with an activated oxalic acid agent in the presence of a base to produce a compound of formula 5

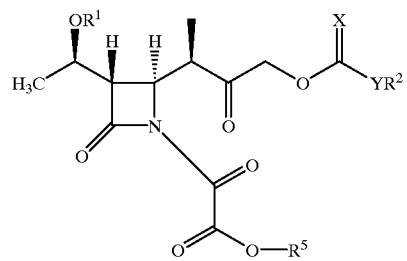

and reacting a compound of formula 5, wherein $R^1$, $R^2$, $R^5$, X and Y are as previously described with a phosphite or phosphonite reagent to produce a compound of formula 6.

Another aspect of the process that is of particular interest is the synthesis of a compound of formula 5:

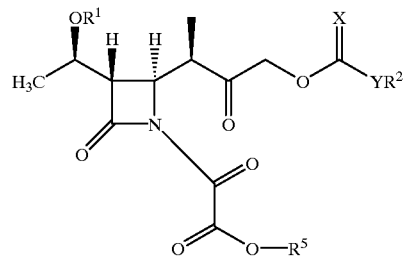

wherein $R^1$ represents H or a suitable protecting group for an alcohol; $R^2$ represents a benzyl, $C_{1-6}$ alkyl or aryl; Y represents $C_{1-3}$ alkyl, O, NH or S; X represents O, NH, or S and $R^5$ represents a carboxy protecting group, comprising reacting a compound of formula 1:

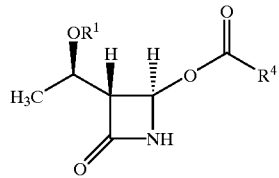

1 wherein $R^1$ is described above and $R^4$ represents $C_{1-15}$ alkyl, aryl or $C_{1-6}$ aralkyl;

with a compound of formula 3:

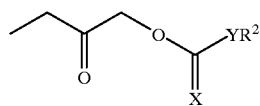

3 wherein $R^2$, X and Y are as previously defined in the presence of $WZ_4$ and an amine to produce a compound of formula 2:

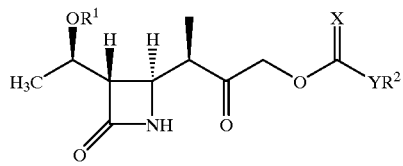

2 wherein W is a titanium, zirconium or hafnium metal and Z represents halo, sulfonate, alkoxy, aryloxy or combination thereof, and $R^1$, $R^2$, X and Y are as previously described, and reacting a compound of formula 2 with an oxalimide forming agent in the presence of a base to produce a In compound of formula 5.

Suitable amines includes trialkylamines such as triethylamine, tributylamine, trimethylamine, ethyldimethylamine, tri-n-propylamine, di-isopropylethylamine, aniline, N,N-di-$C_{1-6}$-alkylanilines such as N,N-diethylaniline and the like.

Suitable bases include trialkylamines such as triethylamine, trimethylamine, ethyldimethylamine, tri-n-propylamine and the like, 1,8-diazabicyclo[5.4.0.]undec-7-ene (DBU), pyridine, imidazole, lutidine, collidine, 4-dimethylaminomethylpyridine, inorganic carbonates and bicarbonates such as sodium carbonate, sodium bicarbonate, potassium bicarbonate, potassium carbonate, and the like and tartrates such as potassium sodium tartrate, potassium tartrate, potassium bitartrate, sodium tartrate, sodium bitartrate and the like, preferably pyridine, lutidine or collidine.

Suitable phosphites include $P(OR^a)(OR^b)(OR^c)$; $P(OR^a)(OR^b)(NR^cR^d)$; $P(R^a)(R^b)(R^c)$; catechol phosphites or catechol dimer phosphites, wherein $R^a$, $R^b$, $R^c$ and $R^d$ may be the same or different and represent a straight or branched chain $C_{1-6}$ alkyl or a phenyl, both of which may be optionally substituted with, for example, a $C_{1-3}$ alkyl. Preferable phosphites are trialkylphosphites such as triethyl phosphite, tributyl phosphite, triisopropyl phosphite, trimethyl phosphite and the like, most preferably triethylphosphite.

Suitable phosphonites include $P(OR^e)(OR^f)(R^g)$, wherein $R^e$ and $R^f$ independently represent $C_{1-4}$ alkyl, allyl, benzyl or phenyl, optionally substituted with $C_{1-3}$ alkyl or $C_{1-3}$ alkoxy and $R^g$ presents $C_{1-4}$ alkyl, trifluoromethyl or phenyl, which is optionally substituted with $C_{1-3}$ alkyl or $C_{1-3}$ alkoxy.

Suitable activated oxylic acid agents include acid and carbodiimide moieties such as oxalyl chloride and benzyl oxalyl chloride.

In particular, processes of interest are those described above wherein $R^1$ represents an alcohol protecting group selected from the group consisting of: H, TES, TMS, TBDMS, pNB, p-nitrobenzyloxycarbonyl, allyl and allyloxycarbonyl.

Other processes that are of particular interest are those described above wherein $R^5$ represents an carboxylic acid protecting group selected from the group consisting of: p-nitrobenzyl (pNB), trimethylsilyl (TMS), triethylsilyl (TES), tert-butyldimethylsilyl (TBDMS), allyl, p-methoxybenzyl, benzyl, trichloroethyl, 2-trimethylsilylethyl, and the like.

Still other processes that are of particular interest are those described above wherein X represents O.

Still other processes that are of particular interest are those described above wherein Y represents O or $CH_2$.

Still other processes that are of particular interest are those described above wherein Y represents O.

Still other processes that are of particular interest are those described above wherein W represents zirconium metal.

Still other processes that are of particular interest are those described above wherein W represents titanium metal.

Still other processes that are of particular interest are those described above wherein W represents hafnium metal.

Still other processes that are of particular interest are those described above wherein Z represents a halogen, most preferably chloride.

The process of the present invention is illustrated by the following generic scheme:

SCHEME A

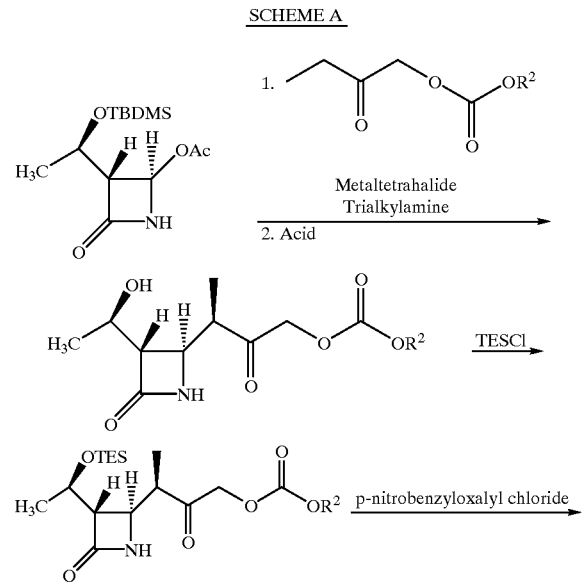

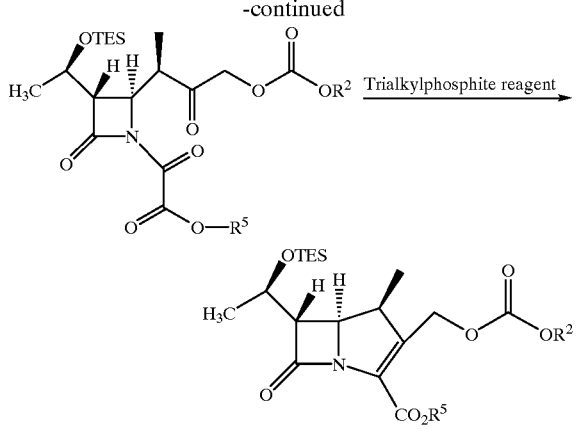

1-Hydroxy-2-butanone is readily available and can be suitably protected by a number of synthetic methods. (3R, 4R)-4-acetoxy-3-[(R)-(tertbutylmethylsilyloxy)ethyl]-2-azetidinone and (3R,4R)-4-acetoxy-3-[(R)-(hydroxyethyl)]-2-azetidinone are both readily available and undergo the addition reaction with high diastereoselectivity and in high yield.

Typical conditions for the reaction involve generation of the titanium, zirconium or hafnium enolate of a suitably protected derivative of 1-hydroxybutanone such as an alkyl or aryl carbonate, preferably ethyl carbonate or isobutylcarbonate. This can be achieved by the addition of the corresponding metal tetrahalide to the derivative of 1-hydroxybutanone followed by addition of a trialkylamine. The stoichiometry of the enolate formation requires at about 0.5 to 3.0 equivalents, preferably 1 to 2.0 equivalents of metal tetrahalide. About 0.5 to about 5 equivalents, preferably about 1 to about 3 equivalents and most preferably about 1 to about 2.0 equivalents of trialkyl amine is used. The enolate generation is generally carried out at a temperature of about −80° C. to about 60° C., preferably about −40° C. to about 30° C.

Generally, the azetidinone is added to the enolate and the reaction temperature warmed to about 0° C.–30° C. The stoichiometry of the reaction requires about 1.0 to about 5 equivalents, preferably about 1 to about 2.0 equivalents of the enolate of the alkyl or aryl carbonate of 1-hydroxybutanone or its synthetic equivalent.

Suitable solvents for the reaction include aromatic solvents such as benzene, toluene, xylene and the like, ethereal solvents such as tetrahydrofuran (THF), diethyl ether, dioxane and the like and haloalkyl solvents such as 1,2 dichloroethane, dichloromethane, chloroform,and the like, preferably the aromatic solvents.

In a typical reaction, the azetidinone is reacted with, for example, a titanium enolate of the ethyl or isobutyl carbonate of 1-hydroxy-2-butanone, preferably the isobutyl carbonate moiety. The protecting group (e.g. TBDMS) is then preferably removed by the addition of an acid such as hydrofluoric acid (HF), HCl, or fluorosilicic acid ($H_2SiF_6$) and subsequently reprotected with another alcohol protecting group (e.g. TES derivative, typically using TESCl, benzyl ethers or allyl ethers), in the presence of a base such as imidazole or pyridine. Reaction with p-nitrobenzyloxalyl chloride affords the oxalimide, the precursor to the cyclization step. The cyclization step typically involves reacting the oxalimide in the presence of a phosphite or phosphonite reagent, preferably a trialkylphosphite agent. The stoichiometry of the cyclization requires from about 2 to about 6 equivalents, preferably about 2.5 to about 5 equivalents of the phosphite or phosphonite. The cyclization is generally carried out at a temperature of about 25° C. to about 200° C., depending on the nature of the phosphorus reagent used. When using a trialkylphosphite reagent the temperature is generally about 90° C. to about 160° C.

The carbapenem produced in the cyclization is a key intermediate in the synthesis of anti-MRSA carbapenem antibiotics and can be readily coupled to a wide range of functional groups in via methods taught in U.S. Ser. No. 08/825,786 now U.S. Pat. No. 5,765,725.

The final product may be characterized structurally by techniques such as NMR, IR, MS, and UV. For ease of handling, the final product, if not crystalline, may be lyophilized from water to afford an amorphous, easily handled solid.

The compounds of the present invention are valuable intermediates for antibacterial agents that are active against various Gram-positive and to a lesser extent Gram-negative bacteria, and accordingly find utility in human and veterinary medicine.

Many of the compounds that can be made in accordance with the present invention are biologically active against MRSA/MRCNS. In vitro antibacterial activity is predictive of in vivo activity when the compounds are administered to a mammal infected with a susceptible bacterial organism.

The invention is further described in connection with the following non-limiting examples.

EXAMPLE 1

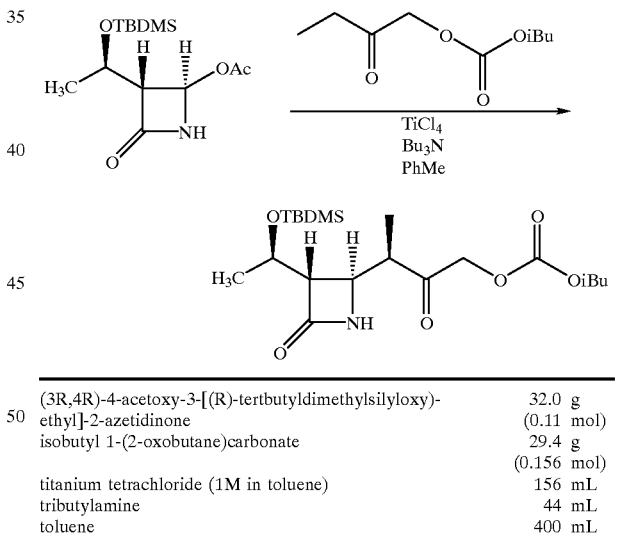

| | |
|---|---|
| (3R,4R)-4-acetoxy-3-[(R)-tertbutyldimethylsilyloxy)-ethyl]-2-azetidinone | 32.0 g (0.11 mol) |
| isobutyl 1-(2-oxobutane)carbonate | 29.4 g (0.156 mol) |
| titanium tetrachloride (1M in toluene) | 156 mL |
| tributylamine | 44 mL |
| toluene | 400 mL |

Titanium tetrachloride solution was added to a solution of the isobutyl carbonate in toluene at −40° C. Tributylamine was added. The acetoxy azetidinone was then added and the reaction stirred at room temperature. After 3 hours the reaction was quenched with dilute hydrochloric acid. The toluene layer was washed with dilute HCl. The toluene layer was used in the subsequent step.

Isolated prod, 13C NMR (CDCl3) δ −5.0, −4.3, 11.7, 17.9, 18.8, 22.5, 25.8, 27.8, 44.6, 51.0, 61.7, 65.4, 69.8, 74.8, 154.8, 168.3, 205.65

EXAMPLE 2

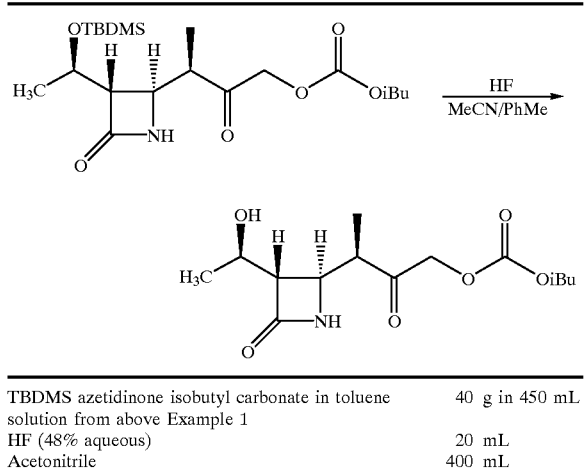

| | |
|---|---|
| TBDMS azetidinone isobutyl carbonate in toluene solution from above Example 1 | 40 g in 450 mL |
| HF (48% aqueous) | 20 mL |
| Acetonitrile | 400 mL |

To the toluene solution from Example 1 was added acetonitrile and the HF solution. After 6 hours the reaction was quenched with aq. Rochelles salt. The toluene layer was dried and the solvent was removed. The crystalline product was swished with hexanes and filtered to yield 4-[3-((1-oxy-2-oxobutane)isobutyl carbonate)]-2-azetidinone (23.3 g) as a white solid.

1H NMR δ0.95 (d, 6H), 1.25 (d, 3H), 1.3 (d, 3H), 2.0 (m, 1H), 2.9 (m, 2H), 3.85 (m, 1H), 3.9 (d, 2H), 4.1 (m, 1H), 4.75 (m, 2H), 6.3 (s, 1H)

EXAMPLE 3

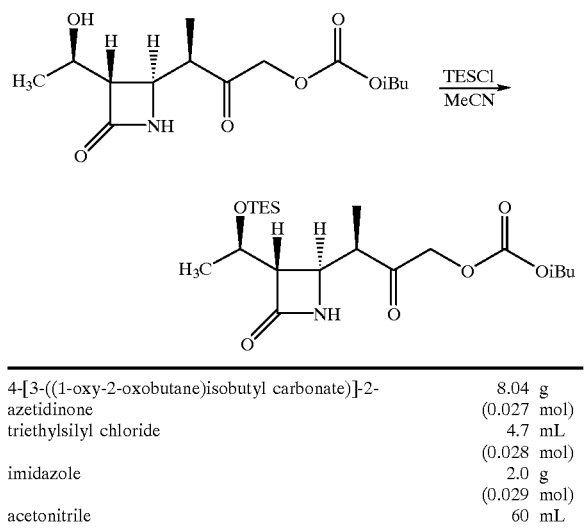

| | |
|---|---|
| 4-[3-((1-oxy-2-oxobutane)isobutyl carbonate)]-2-azetidinone | 8.04 g (0.027 mol) |
| triethylsilyl chloride | 4.7 mL (0.028 mol) |
| imidazole | 2.0 g (0.029 mol) |
| acetonitrile | 60 mL |

To a slurry of the azetidinone in acetonitrile was added imidazole. The reaction became homogeneous and triethylsilyl chloride was added. After 2 hours the reaction was given an aqueous work up and the organics were concentrated in vacuo to afford 11.0 g of TES azetidinone isobutyl carbonate.

1H NMR δ0.5 (q, 9H), 0.9 (t, 6H), 0.9 (d, 6H), 1.2 (2 doublets, 6H), 2.0 (m 1H), 2.9 (m, 2H), 3.8 (m, 1H), 3.9 (d, 2H), 4.1 (m, 1H), 4.7 (m, 2H), 6.4 (s, 1H)

EXAMPLE 4

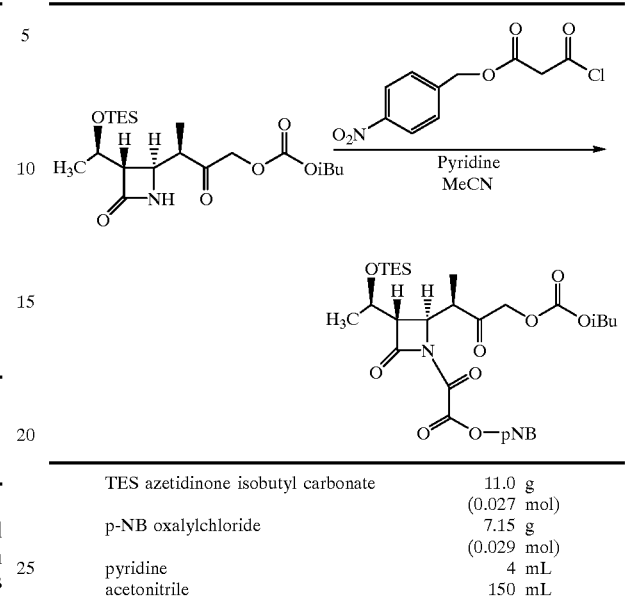

| | |
|---|---|
| TES azetidinone isobutyl carbonate | 11.0 g (0.027 mol) |
| p-NB oxalylchloride | 7.15 g (0.029 mol) |
| pyridine | 4 mL |
| acetonitrile | 150 mL |

Pyridine was added to a solution of pNB oxalylchloride in acetonitrile. After 20 minutes the TES azetidinone isobutyl carbonate was added. The reaction was given an aqueous work up, the organics were concentrated in vacuo to afford TES oxalimide isobutyl carbonate (15.2 g) as a white solid.

13C NMR δ4.8, 6.7, 14.0, 18.8, 22.5, 27.8, 40.9, 54.4, 61.3, 64.7, 66.7, 69.9, 74.8, 123.8, 129.0, 141.2, 148.0, 154.7, 156.0, 159.4, 164.9, 204.6.

EXAMPLE 5

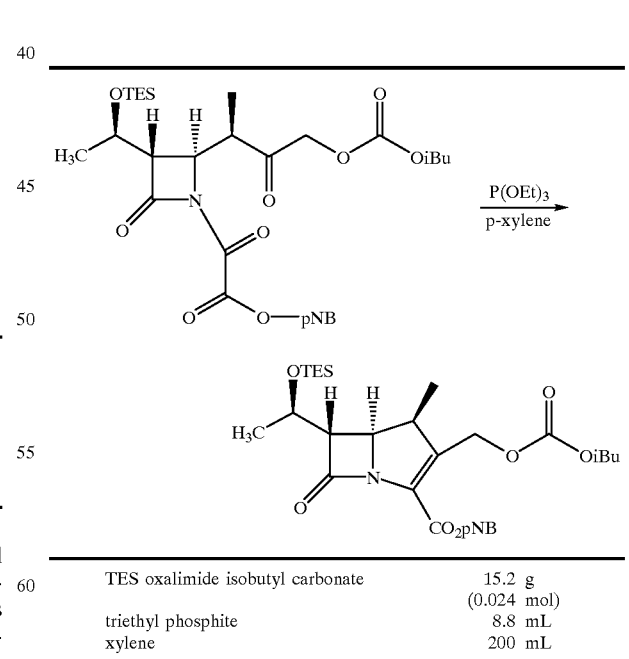

| | |
|---|---|
| TES oxalimide isobutyl carbonate | 15.2 g (0.024 mol) |
| triethyl phosphite | 8.8 mL |
| xylene | 200 mL |

Triethyl phosphite was added to a solution of TES oxalimide isobutyl carbonate in xylene. The reaction was heated to 135° C. for 3 hours. The reaction was given several aqueous washes, dried and the solvent removed in vacuo to afford the desired compound (12.2 g).

$^1$H NMR (399.87 MHz, CDCl$_3$) d 8.22 (m, 2H), 7.66 (m, 2H), 5.57 (d, J=14.5, 1H), 5.46 (d, J=13.7, 1H), 5.27 (d, J=13.7, 1H), 4.83 (dd, J=14.5, 1.2, 1H), 4.26 (overlapping m, 2H), 3.95 (d, J=6.8, 2H), 3.33 (m, 1H), 3.28 (dd, J=5.6, 3.2, 1H), 1.99 (m, 1H), 1.26 (d, J=6.0, 3H), 1.20 (d, J=7.2, 3H), 0.95 (t, J=8.0, 9H), 0.60 (m, 6H)

$^{13}$C NMR (100.55 MHz, CDCl$_3$) d 174.8, 160.4, 155.0, 147.7, 145.5, 142.6, 128.4, 128.1, 123.7, 74.5, 65.7, 65.5, 61.6, 60.7, 55.9, 40.3, 27.8, 22.5, 18.8, 15.3, 6.7, 4.9

What is claimed is:

1. A process of synthesizing a compound of formula 2:

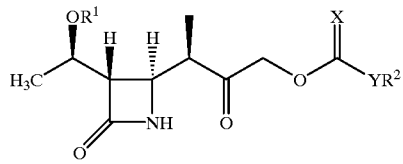

is disclosed wherein R$^1$ represents H or a suitable protecting group for an alcohol; R$^2$ represents a benzyl, C$_{1-6}$ alkyl or aryl; Y represents C$_{1-3}$ alkylene, O, NH or S; and X represents O, NH, or S comprising reacting a compound of formula 1:

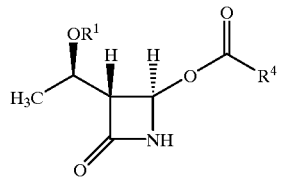

wherein R$^1$ is described above and R$^4$ represents C$_{1-15}$ alkyl, aryl or aralkyl; with a compound of formula 3:

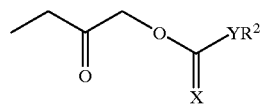

wherein R$^2$, X and Y are as previously defined in the presence of WZ$_4$ and an amine to produce a compound of formula 2, wherein W is a titanium, zirconium or hafnium and Z represents halo, sulfonate, alkoxy, aryloxy or combination thereof.

2. A process of synthesizing a compound of formula 5:

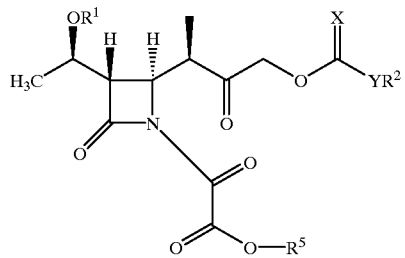

wherein R$^1$ represents H or a suitable protecting group for an alcohol; R$^2$ represents a benzyl, C$_{1-6}$ alkyl or aryl; Y represents C$_{1-3}$ alkylene, O, NH or S; X represents O, NH, or S and R$^5$ represents a carboxy protecting group, comprising reacting a compound of formula 2:

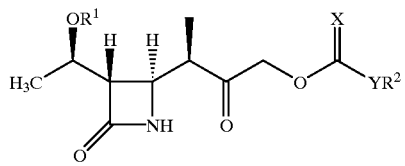

wherein R$^1$, R$^2$, X and Y are as previously described, with an activated oxalic acid agent in the presence of a base to produce a compound of formula 5.

3. A process of synthesizing a compound of structural formula

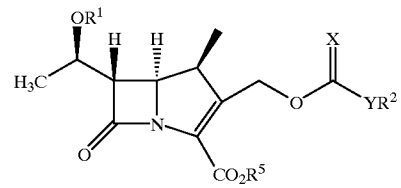

is disclosed wherein R$^1$ represents H or a suitable protecting group for an alcohol; R$^2$ represents a benzyl, C$_{1-6}$ alkyl or aryl; Y represents C$_{1-3}$ alkyl, O, NH or S; X represents O, NH, or S and R$^5$ represents a carboxy protecting group, comprising reacting a compound of formula 5:

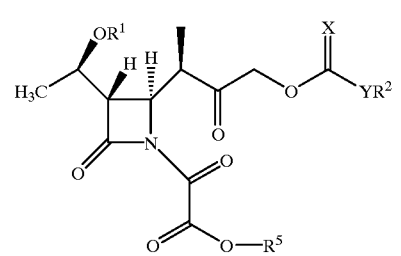

wherein R$^1$, R$^2$, R$^5$, X and Y are as previously described with a phosphite or phosphonite reagent to produce a compound of formula 6, wherein the phosphites belong to the group consisting of P(OR$^a$)(OR$^b$)(OR$^c$); P(OR$^a$)

($OR^b$)($NR^cR^d$); catechol phosphites and catechol dimer phosphites, wherein $R^a$, $R^b$, $R^c$ and $R^d$ independently represent a straight or branched chain $C_{1-6}$ alkyl or a phenyl, both optionally substituted with $C_{1-3}$ alkyl and the phosphonite is P($OR^e$)($OR^f$)($R^g$), wherein $R^e$ and $R^f$ independently represent $C_{1-4}$ alkyl, allyl, benzyl or phenyl, optionally substituted with $C_{1-3}$ alkyl or $C_{1-3}$ alkoxy and $R^g$ presents $C_{1-4}$ alkyl, trifluoromethyl or phenyl, which is optionally substituted with $C_{1-3}$ alkyl or $C_{1-3}$ alkoxy.

4. A process of synthesizing a carbapenem compound of formula 6

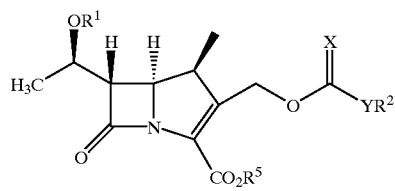

6 wherein $R^1$ represents H or a suitable protecting group for an alcohol; $R^2$ represents a benzyl, $C_{1-6}$ alkyl or aryl; Y represents $C_{1-3}$ alkylene, O, NH or S; X represents O, NH, or S and $R^5$ represents a carboxy protecting group, comprising reacting a compound of formula 2:

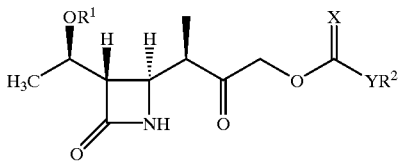

2 wherein $R^1$, $R^2$, X and Y are as previously described, with an activated oxalic acid agent in the presence of a base to produce a compound of formula 5

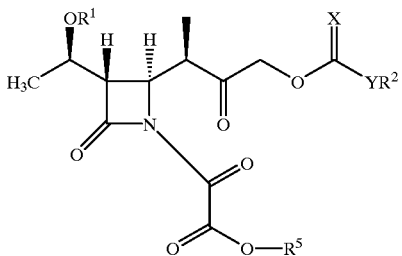

5 and reacting a compound of formula 5, wherein $R^1$, $R^2$, $R^5$, X and Y are as previously described with a phosphite or phosphonite reagent to produce a compound of formula 6, wherein the phosphites belong to the group consisting of P($OR^a$)($OR^b$)($OR^c$); P($OR^a$)($OR^b$)($NR^cR^d$); and catechol phosphites, wherein $R^a$, $R^b$, $R^c$ and $R^d$ independently represent a straight or branched chain $C_{1-6}$ alkyl or a phenyl, both optionally substituted with $C_{1-3}$ alkyl and the phosphonite is P($OR^e$)($OR^f$)($R^g$), wherein $R^e$ and $R^f$ independently represent $C_{1-4}$ alkyl, allyl, benzyl or phenyl, optionally substituted with $C_{1-3}$ alkyl or $C_{1-3}$ alkoxy and $R^g$ presents $C_{1-4}$ alkyl, trifluoromethyl or phenyl, which is optionally substituted with $C_{1-3}$ alkyl or $C_{1-3}$ alkoxy.

5. A process of synthesizing a carbapenem compound of formula 6

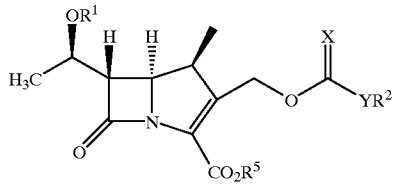

6 wherein $R^1$ represents H, or a suitable protecting group for an alcohol selected from the group consisting of trimethylsilyl (TMS), triethylsilyl (TES), t-butyldimethylsilyl (TBDMS), allyl, allyloxycarbonyl and p-nitrobenzyloxycarbonyl; $R^2$ represents a benzyl, $C_{1-6}$ alkyl or aryl; Y represents $C_{1-3}$ alkylene, O, NH or S; X represents O, NH, or S and $R^5$ represents a carboxy protecting group, comprising reacting a compound of formula 1:

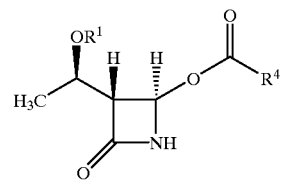

1 wherein $R^1$ is described above and $R^4$ represents $C_{1-15}$ alkyl, aryl or aralkyl; with a compound of formula 3:

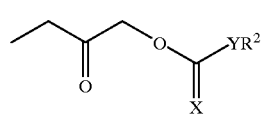

3 wherein $R^2$, X and Y are as previously defined in the presence of $WZ_4$ and an amine to produce a compound of formula 2:

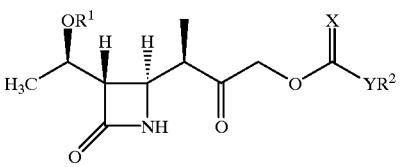

2 wherein W is a titanium, zirconium or hafnium and Z represents halo, sulfonate, alkoxy, aryloxy or combination thereof, and $R^1$, $R^2$, X and Y are as previously described, deprotecting the protecting group $R^1$ and reprotecting with a different alcohol protecting group $R^1$, in the presence of a base, by the addition of an acid selected from the group consisting of hydrofluoric acid (HF), HCl, or fluorosilicic acid ($H_2SiF_6$) and reacting a compound of formula 2 with an activated oxalic acid agent in the presence of a base to produce a compound of formula 5

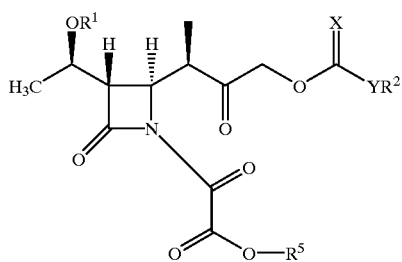

5 and reacting a compound of formula 5, wherein $R^1$, $R^2$, $R^5$, X and Y are as previously described with a phosphite or phosphonite reagent to produce a compound of formula 6, wherein the phosphites belong to the group consisting of $P(OR^a)(OR^b)(OR^c)$; $P(OR^a)(OR^b)(NR^cR^d)$; and catechol phosphites wherein $R^a$, $R^b$, $R^c$ and $R^d$ independently represent a straight or branched chain $C_{1-6}$ alkyl or a phenyl, both optionally substituted with $C_{1-3}$ alkyl and the phosphonite is $P(OR^e)(OR^f)(R^g)$, wherein $R^e$ and $R^f$ independently represent $C_{1-4}$ alkyl, allyl, benzyl or phenyl, optionally substituted with $C_{1-3}$ alkyl or $C_{1-3}$ alkoxy and $R^g$ presents $C_{1-4}$ alkyl, trifluoromethyl or phenyl, which is optionally substituted with $C_{1-3}$ alkyl or $C_{1-3}$ alkoxy.

6. A process of synthesizing a carbapenem compound of formula 5:

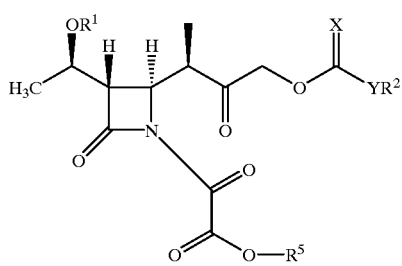

5 wherein $R^1$ represents H, or a suitable protecting group for an alcohol selected from the group consisting of trimethylsilyl (TMS), triethylsilyl (TES), t-butyldimethylsilyl (TBDMS), allyl, allyloxycarbonyl and p-nitrobenzyloxycarbonyl; $R^2$ represents a benzyl, $C_{1-6}$ alkyl or aryl; Y represents $C_{1-3}$ alkylene, O, NH or S; X represents O, NH, or S and $R^5$ represents a carboxy protecting group, comprising reacting a compound of formula 1:

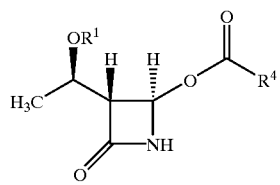

1 wherein $R^1$ is described above and $R^4$ represents $C_{1-15}$ alkyl, aryl or aralkyl; with a compound of formula 3:

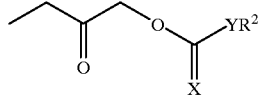

3 wherein $R^2$, X and Y are as previously defined in the presence of $WZ_4$ and an amine to produce a compound of formula 2:

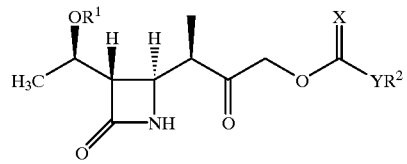

2 wherein W is a titanium, zirconium and hafnium and Z represents halo, sulfonate, alkoxy, aryloxy or combination thereof, and $R^1$, $R^2$, X and Y are as previously described, deprotecting the protecting group $R^1$ and reprotecting with a different alcohol protecting group $R^1$, in the presence of a base, by the addition of an acid selected from the group consisting of hydrofluoric acid (HF), HCl, or fluorosilicic acid ($H_2SiF_6$) and reacting a compound of formula 2 with a activated oxalic acid in the presence of a base to produce a compound of formula 5.

7. A process in accordance with claim 1 wherein $R^1$ represents a member selected from the group consisting of: H, TES, TMS, TBDMS, pNB, (p-nitrobenzyl) p-nitrobenzyloxycarbonyl, allyl and allyloxycarbonyl; $R^5$ represents a carboxylic acid protecting group selected from the group consisting of: p-nitrobenzyl (pNB), benzyl, trimethylsilyl (TMS), triethylsilyl (TES), tert-butyldimethylsilyl (TBDMS), allyl, p-methoxybenzyl, trichloroethyl, and 2-trimethylsilylethyl; $R^2$ represents $C_{1-6}$ alkyl and $R^4$ represents a $C_{1-15}$ alkyl, aryl or aralkyl.

8. A process in accordance with claim 1 wherein X represents O.

9. A process in accordance with claim 1 wherein Y represents O or $CH_2$.

10. A process in accordance with claim 9 wherein Y represents O.

11. A process in accordance with claim 1 wherein W represents zirconium metal.

12. A process in accordance with claim 1 wherein W represents titanium metal.

13. A process in accordance with claim 1 wherein W represents hafnium metal.

14. A process in accordance with claim 1 wherein Z represents a halogen.

15. A process in accordance with claim 14 wherein Z represents chloride.

16. A process in accordance with claim 1 wherein the amine represents triethylamine, tributylamine, trimethylamine, ethyldimethylamine, tri-n-propylamine, di-isopropylethylamine, aniline, and N,N-dialkylanilines.

17. A process in accordance with claim 7 wherein $R^1$ represents a member selected from the group consisting of: H, trimethylsilyl (TMS), triethylsilyl (TES), tert-butyldimethylsilyl (TBDMS), and pNB; $R^5$ represents p-nitrobenzyl (pNB) or benzyl; $R^2$ represents ethyl or isobutyl; and $R^4$ represents alkyl.

18. A process in accordance with claim 1 wherein, after obtaining the compound of formula 2, an acid is added to remove the protecting group followed by addition of another alcohol protecting group $R^{1a}$ to produce a compound of formula 2a

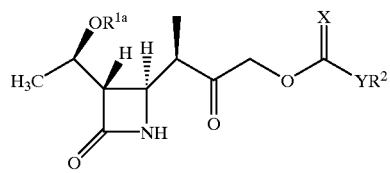

wherein $R^{1a}$ represents trimethylsilyl (IMS), triethylsilyl (TES), tert-butyldimethylsilyl (TBDMS), or pNB (para-nitrobenzyl) said acid belonging to the group consisting of hydrofluoric acid, hydrochloric acid, and fluorosilicic acid.

19. A compound of structural formula 6

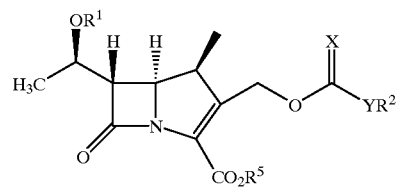

wherein $R^1$ represents H or a suitable protecting group for an alcohol; $R^2$ represents a benzyl, $C_{1-6}$ alkyl or aryl; Y represents $C_{1-3}$ alkylene, O, NH or S; X represents O, NH, or S and $R^5$ represents a carboxy protecting group.

20. A process of synthesizing a compound of formula 2:

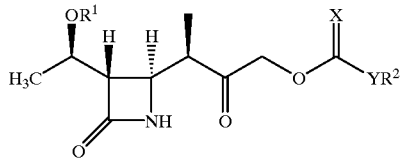

is disclosed wherein $R^1$ represents a member selected from the group consisting of: H, TES(triethylsilyl), TMS(trimethylsilyl), TBDMS(tert-butyldimethylsilyl), and pNB(para-nitrobenzyl); $R^2$ represents ethyl or isobutyl; Y represents O; and X represents O comprising reacting a compound of formula 1:

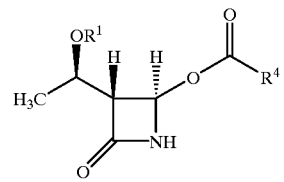

wherein $R^1$ is described above and $R^4$ represents $C_{1-15}$ alkyl, aryl or aralkyl; with a compound of formula 3:

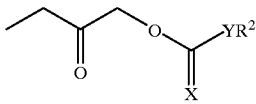

wherein $R^2$, X and Y are as previously defined in the presence of $WZ_4$ and an amine to produce a compound of formula 2, wherein W is a titanium and Z represents chloride.

21. A process in accordance with claim 20 wherein, after reacting formula 1 with formula 3 in the presence of $WZ_4$ and an amine an acid is added to remove the protecting group followed by addition of another alcohol protecting group $R^{1a}$ to produce a compound of formula 2a

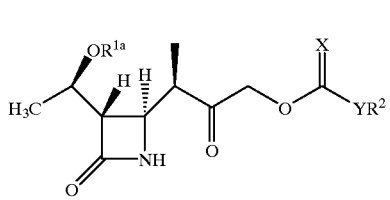

wherein $R^{1a}$ represents trimethylsilyl (TMS), triethylsilyl (TES), tert-butyldimethylsilyl (TBDMS), and pNB (para-nitrobenzyl), X=O, and the acid presents hydrofluoric acid, hydrochloric acid or fluorosilicic acid.

22. A process in accordance with claim 20 wherein the amine represents triethylamine, tributylamine, trimethylamine, ethyldimethylamine, tri-n-propylamine, di-isopropylethylamine, aniline, and N,N-dialkylanilines.

23. A process in accordance with claim 2 wherein the base represents triethylamine, trimethylamine, ethyldimethylamine, tri-n-propylamine, 1,8-diazabicyclo[5.4.0.]undec-7-ene (DBU), pyridine, imidazole, lutidine, collidine, 4-dimethylaminomethylpyridine, sodium carbonate, sodium bicarbonate, potassium bicarbonate, potassium carbonate, potassium sodium tartrate, potassium tartrate, potassium bitartrate, sodium tartrate or sodium bitartrate and the oxalic acid agent represents pNB (p-nitrobenzyl) oxalyl chloride or benzyl oxalyl chloride.

24. A process according to claim 23 wherein the base is pyridine, lutidine or collidine.

25. A compound according to claim 19 which is

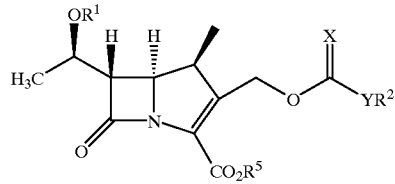

wherein $R^1$ represents a member selected from the group consisting of: H, TES, TMS, TBDMS, and pNB; $R^2$ represents ethyl or isobutyl; Y represents O; and X represents O; and $R^5$ represents p-nitrobenzyl (PNB) or benzyl.

26. A process according to claim 3 wherein the phosphites are trialkylphosphites triethyl phosphite, tributyl phosphite, triisopropyl phosphite, and trimethyl phosphite.

27. A process of synthesizing a carbapenem compound of formula 6

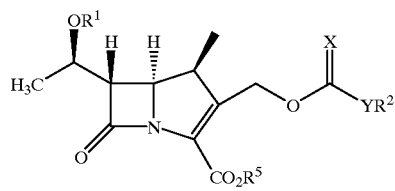

wherein $R^1$ represents a member selected from the group consisting of: H, trimethylsilyl (TMS), triethylsilyl (TES), t-butyldimethylsilyl (TBDMS), and p-nitrobenzyloxycarbonyl (pNB); $R^2$ represents ethyl or isobutyl; Y represents O; and X represents O; and $R^5$ represents p-nitrobenzyl (PNB) or benzyl comprising reacting a compound of formula 1:

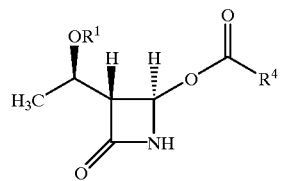

wherein $R^1$ is described above and $R^4$ represents $C_{1-15}$ alkyl, aryl or aralkyl; with a compound of formula 3:

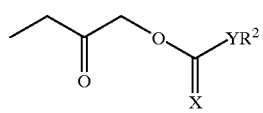

wherein $R^2$, X and Y are as previously defined, in the presence of $WZ_4$ and an amine to produce a compound of formula 2, wherein W is a titanium and Z represents chloride to produce a compound of formula 2

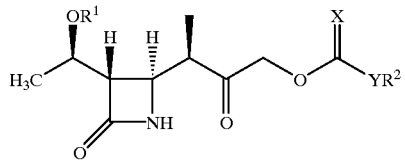

reacting a compound of formula 2 with an pNB(p-nitrobenzyl)oxalyl chloride in the presence of a base such as pyridine, lutidine or collidine to produce a compound of formula 5

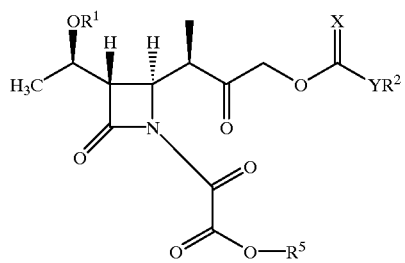

and reacting a compound of formula 5, wherein $R^1$, $R^2$, $R^5$, X and Y are as previously described with triethylphosphite to produce a compound of formula 6.

28. The process in accordance with claim 27, wherein, after obtaining the compound of formula 2, an acid is added to remove the protecting group followed by addition of another alcohol protecting group $R^{1a}$ to produce a compound of formula 2a

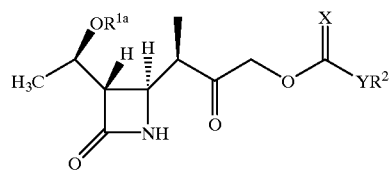

wherein $R^{1a}$ represents trimethylsilyl (TMS), triethylsilyl (TES), tert-butyldimethylsilyl (TBDMS), or pNB (para-nitrobenzyl), and the acid presents hydrofluoric acid, HCl or fluorosilicic acid, then formula 2a is reacted with a pNB (p-nitrobenzyl)oxalyl chloride in the presence of a base and the reaction continued as described in claim 28.

29. A process according to claim 28 wherein the amine represents triethylamine, tributylamine, trimethylamine, ethyldimethylamine, tri-n-propylamine, di-isopropylethylamine, aniline, or N,N-dialkylanilines.

* * * * *